United States Patent
Huber et al.

(10) Patent No.: US 9,285,444 B2
(45) Date of Patent: Mar. 15, 2016

(54) METHOD FOR SUBSTANCE IDENTIFICATION FROM NMR SPECTRUM

(71) Applicant: Numares AG, Regensburg (DE)

(72) Inventors: Fritz Huber, Regensburg (DE); Volker Pfahlert, Kandern (DE); Renate Kirchhoefer, Regensburg (DE); Andreas Krumpel, Regensburg (DE)

(73) Assignee: numares AG, Regensburg (DE)

( * ) Notice: Subject to any disclaimer, the term of this patent is extended or adjusted under 35 U.S.C. 154(b) by 0 days.

(21) Appl. No.: 14/390,044

(22) PCT Filed: Apr. 4, 2013

(86) PCT No.: PCT/EP2013/057104
§ 371 (c)(1),
(2) Date: Oct. 2, 2014

(87) PCT Pub. No.: WO2013/150098
PCT Pub. Date: Oct. 10, 2013

(65) Prior Publication Data
US 2015/0042328 A1 Feb. 12, 2015

Related U.S. Application Data

(60) Provisional application No. 61/620,700, filed on Apr. 5, 2012.

(30) Foreign Application Priority Data

Apr. 5, 2012 (DE) .......................... 10 2012 205 686

(51) Int. Cl.
*G01V 3/00* (2006.01)
*G01R 33/46* (2006.01)
*G01N 24/08* (2006.01)

(52) U.S. Cl.
CPC ............ *G01R 33/4625* (2013.01); *G01N 24/08* (2013.01); *G01R 33/46* (2013.01)

(58) Field of Classification Search
CPC ....................................................... G01R 33/46
USPC .................................. 324/307, 309, 306, 300
See application file for complete search history.

(56) References Cited

U.S. PATENT DOCUMENTS

2006/0217926 A1* 9/2006 Dieterle et al. ................ 702/179
2010/0085050 A1* 4/2010 Dong et al. .................... 324/309
2013/0289887 A1* 10/2013 Huber et al. .................... 702/19

FOREIGN PATENT DOCUMENTS

DE 102010038014 A1 4/2012
EP 2161587 A1 3/2010

OTHER PUBLICATIONS

Barwicz et al. "An Adaptive Rational Filter for Interpretation of Spectrometric Data"; IEEE Transactions on Instrumentation and Measurement; Jun. 2003; pp. 966-9072; vol. 52, No. 3; IEEE Service Center, Piscataway NJ, US.

(Continued)

*Primary Examiner* — Louis Arana
(74) *Attorney, Agent, or Firm* — The Webb Law Firm

(57) ABSTRACT

The present invention relates to a method which allows for an automatic substance identification on the basis of an NMR spectrum. In the scope of the method, determining a multitude of integral ratio values, in each case from at least two integral values of the NMR spectrum, takes place, wherein each integral ratio value specifies the ratio of the height and/or area of the underlying spectral values, and determining a multitude of distance values, in each case from at least two position values of the NMR spectrum, takes place, wherein each distance value specifies the spectral distance between the underlying spectral values. The integral ratio values and the distance values are then used for substance identification.

9 Claims, 4 Drawing Sheets

(56) References Cited

OTHER PUBLICATIONS

McKenzie et al. "Analysis of Complex Mixtures Using High-Resolution Nuclear Magnetic Resonance Spectroscopy and Chemometrics"; Apr. 2011; pp. 336-339; vol. 59, No. 4; Progress in Nuclear Magnetic Resonance Spectroscopy, Pergamon Press, Oxford, GB.

Alam et al. "Development of Variance-Filtered Instrumental Transfer Methods for High-Resolution NMR Spectroscopy"; Feb. 2010; pp. 261-272; vol. 24; Journal of Chemometrics; Wiley Interscience.

Vu et al. "An Integrated Workflow for robust alignment and simplified quantitative analysis of NMR spectrometry data"; BMC Bioinformatics, Oct. 2011; p. 405; vol. 12; No. 5; Biomed Central, London, GB.

* cited by examiner

METHOD FOR SUBSTANCE IDENTIFICATION FROM NMR SPECTRUM

CROSS-REFERENCE TO RELATED APPLICATIONS

This application is the United States national phase of International Application No. PCT/EP2013/057104 filed Apr. 4, 2013, and claims priority to German Patent Application No. 10 2012 205 686.6 and U.S. Provisional Application No. 61/620,700, both filed Apr. 5, 2012, the disclosures of which are hereby incorporated in their entirety by reference.

BACKGROUND OF THE INVENTION

1. Field of the invention

The present invention relates to a method for the identification of a substance in a sample as well as to a software product, containing a software suitable for executing such a method.

2. Description of Related Art

In the field of nuclear magnetic resonance spectroscopy (NMR spectroscopy) the problem has existed for decades that it is not possible to perform an automatic identification of substances contained in a sample with the help of a measured NMR spectrum. Rather, even today NMR spectra still have to be evaluated with great effort by hand in order to be able to identify the substances measured by means of NMR spectroscopy. The success of the identification here depends significantly on the technical expertise of the person performing the manual substance identification. Moreover, the complexity of the composition of the sample which is measured by NMR spectroscopy is also important. In this way, the individual components of a complexly composited sample can generally not be unequivocally, quickly and simply identified with the help of a joint NMR spectrum.

Protons and other NMR-active nuclei, such as for example $^{15}N$ or $^{13}C$, basically produce a defined NMR signal in a defined chemical environment (that is in a specific molecular group of a molecule). Thus, each substance has an individual NMR fingerprint. However, these NMR fingerprints strongly vary depending on the pH value, the temperature, the field strength, the salt concentration and many other parameters. Moreover, the individual NMR fingerprints of different substances contained in a sample often overlap to form complex patterns, from which the individual NMR fingerprints can no longer be readily isolated.

As a result, it has hitherto not been possible to take into account all these factors when it comes to the complex compositions of many substances or to store the various influences of the aforementioned parameters on the individual substances in a database. Because for this purpose extensive series of measurements with various pH values, temperatures, salt concentrations and other parameters would have to be measured for each individual substance. Moreover, it would have to be taken into account that the behaviour of a substance can change depending on the presence of other substances.

DE 10 2010 038 014 A1 describes a method for characterizing a sample comprising the following steps: providing at least one analysis result having a plurality of values, wherein the analysis result was generated by the analysis of a sample by at least one analysis method; determining the value of at least one mathematic relation between at least two values of the plurality of values; generating a characterizing signature of the sample on the basis of the value of the at least one mathematic relation. Thus, this method is directed to characterize a sample—i.e. a complex mixture of different substances—as such. In doing so, it is not relevant to identify the individual substances contained in the sample this—explicitly stated on several passages of DE 10 2010 038 014 A1.

EP 2 161 587 A1 describes a method for automatic analysis of NMR spectra that makes use of a parameter-free interpretation system imitating human logic. This method extracts information from an NMR spectrum in a similar manner like human experts would do this. Thereby, different expert systems are combined which provide distinct NMR spectral features as well as features of a proposed chemical structure. After several iterative method cycles a list of probability weighted hypotheses is generated.

Vu et al.: "An integrated workflow for robust alignment and simplified quantitative analysis of NMR spectrometry data", BMC Bioinformatics 2011, 12: 405 describe a classical adaptation method for spectra during which a reference spectrum is adapted onto a sample spectrum by modification. In doing so, an algorithm is used which is based on a hierarchical cluster-based peak assignment. This method is strongly dependent on the measurement conditions under which the NMR sample spectrum and the NMR reference spectrum have been recorded.

SUMMARY OF THE INVENTION

An object underlying the present invention is to specify a method with which an automatic substance identification for an NMR spectrum can be performed. This method shall here be suitable for NMR spectra which have been recorded under the most various basic conditions.

Such a method for the identification of a substance in a sample has the subsequently explained steps.

First, an NMR spectrum of a sample containing at least one substance having at least one NMR-active nucleus is provided. Suitable NMR-active nuclei are for example $^{1}H$, $^{13}C$ and $^{15}N$.

Afterwards, a line separation of the NMR spectrum takes place. That is, the NMR spectrum is split into discrete spectral values. Such a spectral value can for example be a spectral line corresponding to an individual NMR-active chemical group. Each spectral value here has an integral value and a position value. The integral value specifies the height and/or the area of an individual line of the NMR spectrum or else of an individual spectral section of the NMR spectrum. The integral value thus comprises information on the intensity of the line considered or of the considered spectral section or consists of this intensity information. Each position value specifies the position of the line considered or of the considered spectral section in the NMR spectrum. The position values are here a measure for the magnetic shielding of individual molecular groups/atoms in the entire molecule of the substance contained in the sample. The integral values are a measure for the number of individual molecular groups/atoms in the NMR spectrum.

As position, usually the central or mean position of the line considered or of the considered spectral section is used here. In technical terms such a spectral section is also referred to as "bin". The separation or the cutting of an NMR spectrum into various discrete spectral sections, in each case comprising one or multiple lines, is hence also known to a person skilled in the art under the technical term "to bin".

The line separation can basically take place according to methods generally known to a person skilled in the art. Basically, any method suitable for extracting information about individual molecular groups or atoms from an NMR spectrum can be employed. The line separation specified in this case tries to illustrate an NMR spectrum as an overlapping, as perfect as possible, of Lorenz curves (or of a sum of Lorenz and Gauss curves). The objective pursued here is to preferably allocate a defined integral value and a corresponding position value to each individual NMR-active group after the line separation. That is, preferably each line of the NMR spectrum is separated from each other line of the NMR spectrum.

Afterwards, on the basis of in each case at least two integral values of the NMR spectrum a multitude of integral ratio values is calculated. Preferably, each individual integral value of the NMR spectrum is set off against every other integral value of the NMR spectrum. Each integral ratio value here specifies the ratio of the height and/or of the area of the underlying spectral values. When, for example, 20 spectral values with 20 integral values are obtained by the line separation and subsequently in each case exactly two integral values are set off against each other to form an integral ratio value, 20×20=400 integral ratio values are obtained. 20 of these integral ratio values have a value of 1 (division of the same integral values by each other) and are preferably not taken into further account as integral ratio values because they contain no relevant information.

Moreover, a multitude of distance values from in each case at least two position values of the NMR spectrum is calculated. Preferably, in this case also, setting off each individual position value of the NMR spectrum against every other position value of the NMR spectrum takes place. Each distance value here mirrors the spectral distance between the underlying spectral values. When, according to the example above, 20 spectral values and correspondingly also 20 position values are obtained and in each case exactly two position values are set off against each other, thus 20×20=400 distance values are obtained. 20 of these distance values have a value of 1 (division of the same position values by each other) and are preferably not taken into further account as distance values because they contain no relevant information.

The spectral distance is a measure for how far individual lines of the NMR spectrum are distanced from each other. When the distance is small, the lines lie close to each other. When the distance is great, the lines are far apart. The spectral distance can be given in various units such as for instance Hz or ppm.

In the claimed method a comparison of the calculated integral ratio values of the NMR spectrum with corresponding integral ratio values of an NMR reference spectrum now takes place. The NMR reference spectrum here is an NMR spectrum of at least one reference substance. For the calculation of the integral ratio values of the NMR reference spectrum, one preferably proceeds analogously to the calculation of the integral ratio values of the examined NMR spectrum. That is, first, particularly a line separation is performed to obtain integral values of multiple, preferably of all, spectral values.

After comparing the integral ratio values, a selection of a first proper subset from the integral ratio values of the NMR spectrum takes place. The first subset here comprises those integral ratio values which correspond to an integral ratio value of the NMR reference spectrum within first tolerance limits that can be given in each case. Whether there is a correspondence or not basically depends on the respective individual case, wherein factors such as for example the number of lines in the considered NMR spectrum, their distance from each other and the absolute value of the considered integral ratio values have to be taken into account. That is, the quality of the data which is to be compared with each other is one of the decisive factors for whether there is a correspondence or not. With high-quality data to be compared (few interferences, small measurement errors, a good signal-to-noise ratio, lines which can well be separated from each other, significant integral ratios etc.) the tolerance limits are to be set lower than with lesser-quality data. Preferably, the tolerance limits or the still permissible errors are selected in such a way that no right candidates are excluded by mistake. That is, false negative results shall be avoided.

For example, when all integral ratios with the exception of one integral ratio value of an NMR reference spectrum fall within the range of about 1 and the only remaining integral ratio value lies in the range of 10, there can be a correspondence when in the NMR spectrum of the sample likewise all integral ratio values but one integral ratio value fall within the range of about 1 (and have no relevant deviations from the integral ratio values of the NMR reference spectrum) and the remaining integral ratio value is 20. On the other hand, such a deviation of 100% can no longer be classified as correspondence in other case constellations with less significant integral ratio values.

In other words, the decision whether there is a correspondence or not takes place with the help of individual criteria. Preferably, these criteria are determined according to whether a known substance in an NMR spectrum is actually identified as this substance when a comparison of the NMR spectrum of a sample containing this substance with an NMR reference spectrum of this substance takes place.

Preferably, it is proceeded on the assumption that there is a correspondence when an integral ratio value of the NMR spectrum deviates from an integral ratio value of the NMR reference spectrum by 100% or less, particularly 50% or less, particularly 40% or less, particularly 30% or less, particularly 20% or less, particularly 15% or less, particularly 10% or less, particularly 5% or less, particularly 4% or less, particularly 3% or less, particularly 2% or less, particularly 1% or less and very particularly 0.5% or less. A respective particular deviation of a corresponding integral ratio value of the NMR reference spectrum can here be taken as a basis for each integral ratio value of the NMR spectrum to be compared. Ideally, there is a correspondence in the case when an integral ratio value of the NMR spectrum is identical to an integral ratio value of the NMR reference spectrum. In the scope of the respective measurement accuracies, however, usually at least the previously mentioned tolerances have to be taken into account.

In the scope of the method claimed a comparison of the distance values of the NMR spectrum with corresponding distance values of the NMR reference spectrum also takes place. The distance values of the NMR reference spectrum here are preferably calculated in the same manner as the distance values of the NMR spectrum of the examined sample. Comparing the distance values serves to select a second proper subset from the distance values of the NMR spectrum. The second subset here comprises those distance values which correspond to a distance value of the NMR reference spectrum within second tolerance limits that can be given in each case. Preferably, it is proceeded on the assumption that there is a correspondence here under the same prerequisites which were explained with reference to the comparison of the integral ratio values. Expressed in relative errors, it is then preferably proceeded on the assumption that there is a correspondence when the deviation between a distance value of the NMR spectrum and a distance value of the NMR reference spectrum is 100% or less, particularly 50% or less, particularly 40% or less, particularly 30% or less, particularly 20% or less, particularly 15% or less, particularly 10% or less, particularly 5% or less, particularly 4% or less, particularly 3% or less, particularly 2% or less, particularly 1% or less and very particularly 0.5% or less. In this case also, a respective particular deviation from a corresponding distance value of the NMR reference spectrum can be taken as a basis for each distance value of the NMR spectrum to be compared. Preferably there is a correspondence between the distance values in the case when a distance value of the NMR spectrum is identical to the distance value of the NMR reference spectrum. But in this case also, in the scope of the measurement accuracy usually at least the aforementioned tolerances have to be taken into account.

When the first subset and the second subset are formed, they are compared with each other. Afterwards, all those integral ratio values and distance values are selected from both subsets which are based on the same spectral values. This selection represents a third proper subset.

As an example, for a more detailed explanation the following case constellation is assumed: The first subset contains a first integral ratio value formed from the integral values of a first and a second spectral value. The first subset, moreover, contains a second integral ratio value formed from the integral values of a third and a fourth spectral value. The second subset contains a first distance value formed from the first spectral value and the second spectral value. The second subset, moreover, contains a second distance value formed from a fifth spectral value and a sixth spectral value. Then the first integral ratio value and the first distance value would be formed from the same spectral values, while the second distance value would be formed from spectral values from which no integral ratio value in the first subset would be formed. In this example the third subset will thus consist of the first integral ratio value or the first distance value. The second integral ratio value and the second distance value, however, would not be contained in the third subset. The third subset thus represents an intersection between the first subset and the second subset.

Finally, a quality criterion of the values contained in the third subset is determined, said criterion resulting from a comparison of these values with the integral ratio values and/or with the distance values of the NMR reference spectrum. With the help of this quality criterion a decision can then be made as to whether the substance contained in the sample is identified as the reference substance or not.

The quality criterion can for example comprise or be a measure for the deviation of the integral ratio values of the NMR spectrum from the integral ratio values of the NMR reference spectrum and/or for the deviation of the distance values of the NMR spectrum from the distance values of the NMR reference spectrum.

In a further embodiment the quality criterion can comprise or be the number of values contained in the third subset in comparison with the number of integral ratio values or distance values of the NMR reference spectrum. When, to calculate the integral ratio values and the distance values, in each case the same number of spectral values is used, the number of integral ratio values and the number of distance values are identical. When the calculation of the integral ratio values is, for example, based on, in each case, exactly two spectral values or on the integral values allocated to these spectral values, $n^2$ integral ratio values are obtained when there are n spectral values. Of these $n^2$ integral ratio values n integral ratio values have exactly a value of 1 (division of two identical integral values by each other). Preferably, these integral ratio values as also the corresponding distance values are not taken into account when determining the number of integral ratio values or distance values. This rule applies both for the considered NMR spectrum of the analyzed sample and for the NMR reference spectrum.

When the number of values contained in the third subset is identical to the number of integral ratio values or distance values of the NMR reference spectrum or when it exceeds them by at least a lower threshold which can be predetermined, the substance contained in the sample can in one embodiment be identified as the reference substance. When, however, the values contained in the third subset are significantly less than integral ratio values or distance values comprised in the NMR reference spectrum, the substance contained in the sample can in one embodiment not be identified as the reference substance. Depending on the number of values contained in the third subset, however, for example the statement can be made that the substance contained in the sample is at least not the reference substance. In order to be able to unequivocally identify the substance contained in the sample in such a case, some of the aforementioned steps of the method should be performed again preferably with a new NMR reference spectrum.

In order to not distort the informative value of the number of integral ratio values or distance values of the NMR spectrum, the integral ratio values and the distance values of the NMR reference spectrum should be calculated in each case from the same number of spectral values (e.g. in each case exactly two spectral values) as the integral ratio values and the distance values of the NMR spectrum of the examined sample.

The quality criterion can preferably take into account various parameters. It is thus conceivable that, when there is little correspondence between the number of values of the third subset and the number of integral ratio values or of distance values of the NMR reference spectrum, a substance identification nevertheless takes place when at the same time only a small deviation between the compared integral ratio values and/or distance values has been ascertained. By the same token, greater deviations of the compared integral ratio values and/or distance values can be compensated for when there is a higher correspondence between the number of values of the third subset and the number of integral ratio values or distance values of the NMR reference spectrum. The quality of the values of the third subset can thus take into account qualitative and quantitative aspects of the values.

The present method is based on measuring two properties of a molecule which are independent of each other with the same measuring method. Herein, on the one hand, it is the number of the molecular groups and their proton ratios in the entire molecule to which said number of molecular groups and their proton ratios an NMR signal can be allocated. This property is expressed by the integral value. On the other hand, here it is the magnetic shielding of individual molecular groups in the entire molecule. This property is expressed by the position value of each spectral value.

What is special about the present method is that it can be performed independently of the respective measurement conditions. That is, otherwise most critical parameters such as for instance the pH value, the temperature, the salt concentration or the magnetic field strength, under which an NMR measurement is performed, are practically no longer of importance for the evaluation and can be processed automatically. It is also possible that the NMR reference spectrum has been recorded with other parameters than the NMR spectrum of the sample containing the substance to be identified. That ensures a global applicability of the present method independent of individual instruments. Applying the presently claimed method, an unequivocal identification of a substance in a sample by means of NMR spectroscopy can thus take place by means of a database, set up once, with NMR reference spectra of reference substances.

Alternatively, a substance can also be identified by means of its molecular structure based on theoretical foundations insofar as individual molecular groups of this substance have been identified by the present method.

A user's intervention in the method is not required here. Rather, the method can be performed fully automatically, so that an automatic or automated substance identification is possible even in complex substance mixtures.

Although the NMR reference spectrum can be a spectrum of different substances, in a preferable embodiment of the method the NMR reference spectrum is a spectrum of exactly one individual reference substance.

In one variant the substance contained in the sample is then identified as the reference substance, when at least 60% of the integral ratio values or of the distance values of the NMR reference spectrum are contained in the third subset. In further preferable embodiments a value of 70%, particularly 75%, particularly 80%, particularly 85%, particularly 90%, particularly 95% and very particularly 99% is selected as lower threshold value for the unequivocal identification of the substance as reference substance. In a further preferable embodiment of the method the substance is unequivocally identified not to be the reference substance when less than 40%, particularly less than 30%, particularly less than 20%, particularly less than 10% and very particularly less than 5% of the integral ratio values or of the distance values of the NMR reference spectrum are contained in the third subset. As explained above, the aforementioned limits can be exceeded upwards or downwards insofar as, when it comes to the quality criterion, additional information about the values of the third subset is taken into account.

The aforementioned individual steps of the method here do not necessarily have to be performed in the previously explained sequence. Rather, for example, comparing the integral ratios and selecting the first subset could take place directly after determining the multitude of integral ratio values. Equally, for example, comparing the distance values and selecting a second subset could take place directly after determining the multitude of distance values. For a person skilled in the art it goes without saying that the step of comparing the first subset with the second subset can be performed only when the first subset and the second subset have been formed.

In a further variant the above explained steps of comparing the integral ratio values, selecting a first subset, comparing the distance values, selecting a second subset, comparing the first subset with the second subset and deciding whether the substance contained in the sample is identified as reference substance are repeated so often until all the substances contained in the sample have unequivocally been identified with the help of the reference substances or else there no longer are further NMR reference spectra. Here, in each step of the repetition another NMR reference spectrum, preferably of another reference substance, is used for the respective comparative purposes. In this manner it is possible to allocate the various substances contained in the sample to different reference substances by a corresponding iterative method. The only prerequisite for this is that there already are NMR reference spectra for the individual reference substances. The NMR reference spectra can be generated by measurement, by simulation or by other methods. These NMR reference spectra are preferably stored in a database.

The distance values can basically be determined by any suitable method which permits characterizing the resonance properties of the spectral values considered.

Preferably, the distance values are calculated as direct differences of the position values, as standardized differences of the position values or as quotient of the position values.

Taking into account absolute position values, one can work with the direct differences of resonance frequencies ($v_a=T+\Delta v_a$). T here refers to the carrier frequency (also referred to as operating frequency or proton resonance frequency) of the NMR spectrometer used. $\Delta v_a$ refers to the natural frequency share of the respective signal appertaining to a substance A.

Alternatively, the use of standardized differences of resonance frequencies is recommendable for calculating the distance values, wherein the position values are then no longer expressed in Hz but in ppm. Finally, unequivocally determining the distance of two peaks or lines from each other is also possible via forming a quotient. An unequivocal allocation of distance via ratios is possible in this case because the carrier frequency is much greater than the natural frequency shares of the individual signals ($T \gg \Delta v$).

In one variant the integral ratios are formed from in each case exactly two integral values of the NMR spectrum. Alternatively, or supplementary to this, preferably the distance values are also calculated in each case from exactly two position values of the NMR spectrum. When there are n different lines of a substance A, there are $(n^2-n)/2$ relevant integral ratios between in each case two lines and exactly as many relevant distance values between in each case two lines. Based on $n^2$ integral ratios or distance values preferably n values having a value of 1 are subtracted, according to the considerations explained above. The subsequent division of the remaining group of values is divided by 2, as half of the respective values corresponds to the reciprocal value of the other half of the values. Consequently, the number of relevant integral ratio values or distance values is only less than half the number of all the integral ratio values or distance values. The distance values can also be referred to as peak distances or line distances.

The use of exactly two integral values or of exactly two position values to determine corresponding integral ratio values or distance values has the advantage that in this case the information contained in the integral ratio values and distance values is not too complex, but can still be attributed to the underlying spectral values in a comparably simple manner. This facilitates performing the method.

In a further variant the substance contained in the sample is not only qualitatively identified as a specific substance, but is also quantified. That is, in this variant the concentration of the substance contained in the sample is detected. In order to permit such a quantification, the substance first must have been identified in a qualitative manner. When this has taken place, it is also known which NMR reference spectrum can be used to quantify the substance contained in the sample. Now, for example, an integral value of the NMR spectrum can be compared with a corresponding integral value of the same spectral value of the NMR reference spectrum. Insofar as the concentration of the substance underlying the NMR reference spectrum is known, the concentration of the substance in the sample can be determined in this manner. For when the proton concentration for an integral value is known, all other integral values can then be converted into proton concentrations from this. When a molecular group is allocated to an integral value or to the corresponding spectral value, its concentration can be calculated from this.

In order to enhance the measurement accuracy it can be recommendable here to compare not only an individual integral value of the NMR spectrum with a corresponding individual integral value of the NMR reference spectrum, but also to compare all the integral values of the NMR spectrum characteristic of the respective considered substance with corresponding integral values of the NMR reference spectrum. Ideally, one should be able to detect the same concentration of the respective considered substance from all spectral values or the corresponding integral values of the spectral values of the NMR spectrum. Actually, however, due to the measurement accuracy smaller deviations between the determined concentrations based on different integral values can be detected, which said deviations can be illustrated in a normally distributed frequency distribution.

In order to be able to perform the conventional evaluation methods according to prior art in as simple a manner as possible, one usually works with decoupled NMR spectra. The present method can also be performed on the basis of decoupled NMR spectra. This is, however, not required. Rather, non-decoupled NMR spectra can also be used in order to be able to perform a substance identification according to the present method. In a preferable variant the method is first performed by using a decoupled NMR spectrum. If, in this manner, an unequivocal substance identification of the substances contained in the sample was not yet possible, the method is afterwards performed again by using a non-decoupled NMR spectrum of the same sample. Although non-decoupled NMR spectra are more complex and hence are more difficult to evaluate according to the traditional methods, it has to be taken into account that they contain more information than decoupled NMR spectra. Thus surplus information can, in a preferable manner, be made use of in the present method to be able to surely and successfully perform a substance identification even in more difficult cases. Preferably, when a decoupled NMR spectrum is analysed a decoupled NMR reference spectrum is employed also. Preferably, when a non-decoupled NMR spectrum is analysed a non-decoupled NMR reference spectrum is employed also.

The object underlying the present invention is also achieved by a software product having a software which has a program code to perform a method according to the previous explanations when the software is run on a computer. Such a software represents the technical solution to the hitherto unsolved technical problem of how to be able to automatically identify different substances contained in a sample as specific substances on the basis of an NMR spectrum. As, to run this software, it is not required to hold available extensive databases with NMR spectra which have been recorded under various conditions, the computational effort when using a corresponding software is reduced considerably. In a very advantageous manner resources, time and money can thereby be saved using a corresponding substance identification. Furthermore, an automatic substance identification in this manner becomes available for NMR spectra measured under various conditions and on various instruments.

The present invention will now be further explained with the help of drawings and examples. In the figures:

DESCRIPTION OF THE INVENTION

The subsequent explanation of the figures is to be understood as exemplary embodiment of the presently specified method, wherein individual steps of the method will be addressed in more detail than others.

Figure 1:
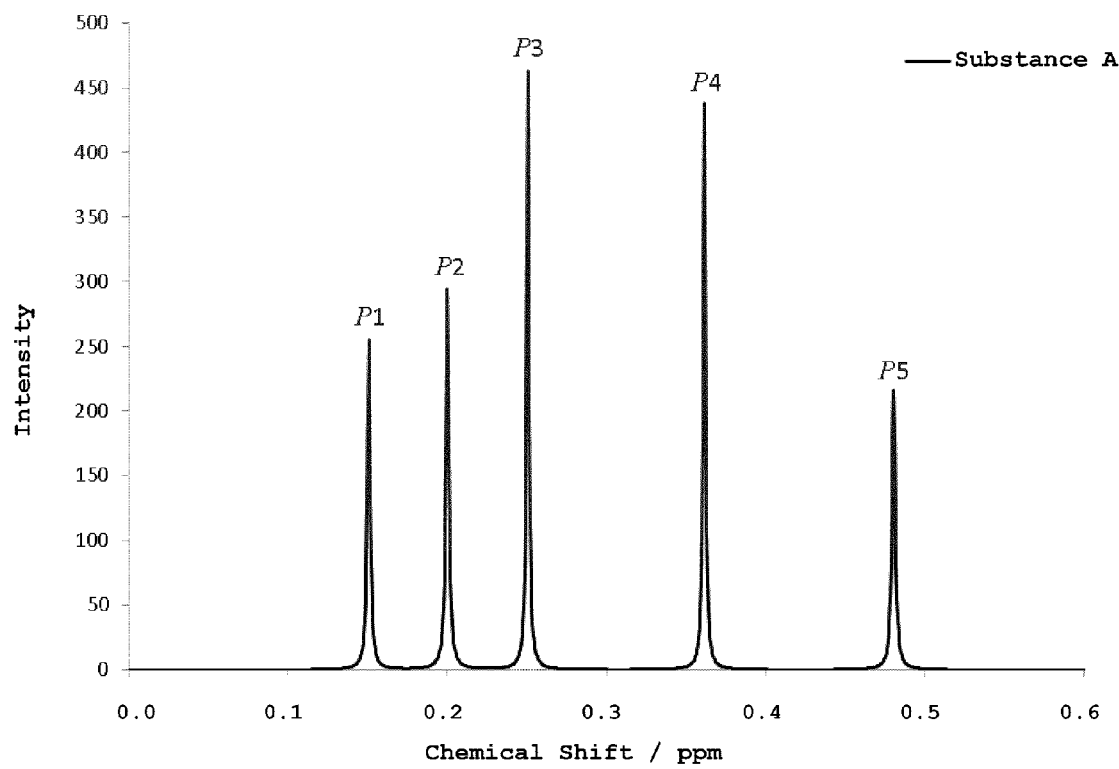
FIG. 1 shows an NMR spectrum of a substance A.

FIG. 1 shows an NMR spectrum of a substance A serving as reference substance. The spectrum shows the intensity, plotted against the chemical shift (measured in ppm), of the individual signals. The spectrum of FIG. 1 has five lines or peaks P1, P2, P3, P4 and P5. Each individual peak of these peaks is characteristic of a molecular group in the entire molecule of substance A. As the individual peaks of the NMR spectrum of FIG. 1 are well separated from each other, no special line separation needs to be performed. Rather, the spectral values of the individual peaks can be deduced directly from the NMR spectrum. Each spectral value consists of an integral value, specifying the area under the individual peaks, and a position value, specifying the chemical shift of the respective considered peak. The subsequent table 1 lists the individual integral values and position values of the five spectral values contained in the NMR spectrum of substance A.

TABLE 1

Integral values and position values of the individual peaks contained in the NMR spectrum of substance A

| Peak | Position | Integral | Width |
|------|----------|----------|-------|
| P1 | 0.151 | 0.826 | 0.0010 |
| P2 | 0.200 | 1.019 | 0.0011 |
| P3 | 0.251 | 1.249 | 0.0009 |
| P4 | 0.362 | 1.178 | 0.0009 |
| P5 | 0.481 | 0.789 | 0.0012 |

As already explained, when there are n different peaks of a substance A there are $(n^2-n)/2$ relevant integral ratios and peak distances or distance values. The distance values can be calculated either (i) as direct differences of resonance frequencies or (ii) as standardized differences of resonance frequencies or (iii) as ratios—by using resonance frequencies written in relation to the carrier frequency—, depending on which scaling is used.

Figure 2:
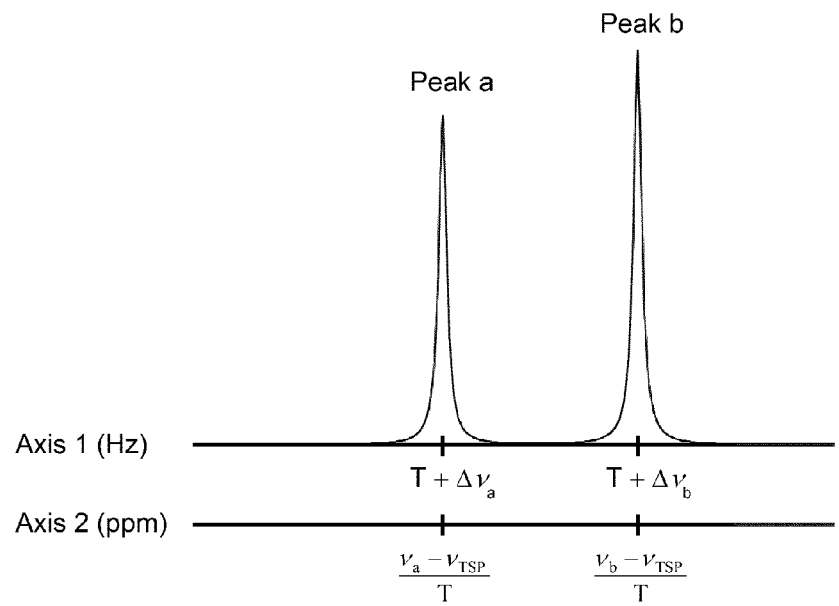
FIG. 2 shows a graphic illustration of two lines of an NMR spectrum to illustrate the calculation of distance values.

FIG. 2 illustrates the various calculation methods for determining the distance values from the position values of the individual peaks of an NMR spectrum. While axis 1 specifies a scaling in Hertz (Hz), axis 2 shows a scaling in ppm. On the basis of the Hertz scaling, direct differences of individual resonance frequencies or quotients of the resonance frequencies can be formed. On the basis of the ppm scale, standardized differences of resonance frequencies can be detected.

The three possibilities of calculating the distance values are subsequently illustrated again by corresponding formulae:

$$\text{direct differences(axis 1): } (T + \Delta v_b) - (T + \Delta v_a) = \quad \text{(i)}$$
$$\Delta v_b - \Delta v_a = v_b - v_a [\text{Hz}]$$

-continued standardized differences (axis 2): $\left(\frac{v_b - v_{TSP}}{T}\right) - \left(\frac{v_a - v_{TSP}}{T}\right) =$ (ii)

$\frac{v_b - v_a}{T}$ [ppm]

distances as quotient (axis 1): $\frac{v_b}{v_a} = \frac{T + \Delta v_b}{T + \Delta v_a}$ $(T \gg \Delta v_{a,b})$ (iii)

Now, on the basis of table 1 first all possible integral ratios, in each case from two integral values, are formed. That is, each integral value is divided by every other integral value. The corresponding calculation basis as well as the concrete results for the integral values of table 1 are illustrated in the subsequent table 2.

TABLE 2

Basis of calculation of calculating integral ratio values from integral values and corresponding results for the integral values of table 1.

| Integral | I1 | I2 | I3 | I4 | I5 |
|---|---|---|---|---|---|
| I1 | I1/I1 | I1/I2 | I1/I3 | I1/I4 | I1/I5 |
| I2 | I2/I1 | I2/I2 | I2/I3 | I2/I4 | I2/I5 |
| I3 | I3/I1 | I3/I2 | I3/I3 | I3/I4 | I3/I5 | = |
| I4 | I4/I1 | I4/I2 | I4/I3 | I4/I4 | I4/I5 |
| I5 | I5/I1 | I5/I2 | I5/I3 | I5/I4 | I5/I5 |

| Integral | 0.83 | 1.02 | 1.25 | 1.18 | 0.79 |
|---|---|---|---|---|---|
| 0.83 | 1.00 | 0.81 | 0.66 | 0.70 | 1.05 |
| 1.02 | 1.23 | 1.00 | 0.82 | 0.87 | 1.29 |

TABLE 2-continued

Basis of calculation of calculating integral ratio values from integral values and corresponding results for the integral values of table 1.

| 1.25 | 1.51 | 1.23 | 1.00 | 1.06 | 1.58 |
| 1.18 | 1.43 | 1.16 | 0.94 | 1.00 | 1.49 |

Now, based on the position values of table 1 the corresponding distances of in each case two peaks are calculated as peak distances or distance values. This is subsequently illustrated as an example according to the second variant (distance values as standardized differences of resonance frequencies) explained above.

TABLE 3

Basis of calculation for calculating distance values as standardized difference of resonance frequencies and results for the position values of table 1.

| ppm | δ1 | δ2 | δ3 | δ4 | δ5 |
|---|---|---|---|---|---|
| δ1 | δ1-δ1 | δ1-δ2 | δ1-δ3 | δ1-δ4 | δ1-δ5 |
| δ2 | δ2-δ1 | δ2-δ2 | δ2-δ3 | δ2-δ4 | δ2-δ5 |
| δ3 | δ3-δ1 | δ3-δ2 | δ3-δ3 | δ3-δ4 | δ3-δ5 | = |
| δ4 | δ4-δ1 | δ4-δ2 | δ4-δ3 | δ4-δ4 | δ4-δ5 |
| δ5 | δ5-δ1 | δ5-δ2 | δ5-δ3 | δ5-δ4 | δ5-δ5 |

| ppm | 0.15 | 0.20 | 0.25 | 0.36 | 0.48 |
|---|---|---|---|---|---|
| 0.15 | 0.00 | −0.05 | −0.10 | −0.21 | −0.33 |
| 0.20 | 0.05 | 0.00 | −0.05 | −0.16 | −0.28 |
| 0.25 | 0.10 | 0.05 | 0.00 | −0.11 | −0.23 |
| 0.36 | 0.21 | 0.16 | 0.11 | 0.00 | −0.12 |

Alternatively, instead of the standardized differences of the resonance frequencies, quotients of the individual resonance frequencies can also be employed to calculate the distance of in each case two peaks. The basis of calculation for this as well as the corresponding results for the position values of table 1 are illustrated in the subsequent table 4.

TABLE 4

Basis of calculation for calculating distance values on the basis of quotients and concrete results for the position values of table 1.

| 16n | | | | | |
|---|---|---|---|---|---|
| — | v1/v1 | v1/v2 | v1/v3 | v1/v4 | v1/v5 |
| v2 | v2/v1 | v2/v2 | v2/v3 | v2/v4 | v2/v5 |
| v3 | v3/v1 | v3/v2 | v3/v3 | v3/v4 | v3/v5 | = |
| v4 | v4/v1 | v4/v2 | v4/v3 | v4/v4 | v4/v5 |
| v5 | v5/v1 | v5/v2 | v5/v3 | v5/v4 | v5/v5 |

| Hz | 600000090.30 | 600000120.00 | 600000150.30 | 600000216.90 | 600000288.30 |
|---|---|---|---|---|---|
| 600000090.30 | 1.000000000 | 0.999999951 | 0.999999900 | 0.999999789 | 0.999999670 |
| 600000120.00 | 1.000000049 | 1.000000000 | 0.999999950 | 0.999999839 | 0.999999720 |
| 600000150.30 | 1.000000100 | 1.000000050 | 1.000000000 | 0.999999889 | 0.999999770 |
| 600000216.90 | 1.000000211 | 1.000000161 | 1.000000111 | 1.000000000 | 0.999999881 |

Figure 3:
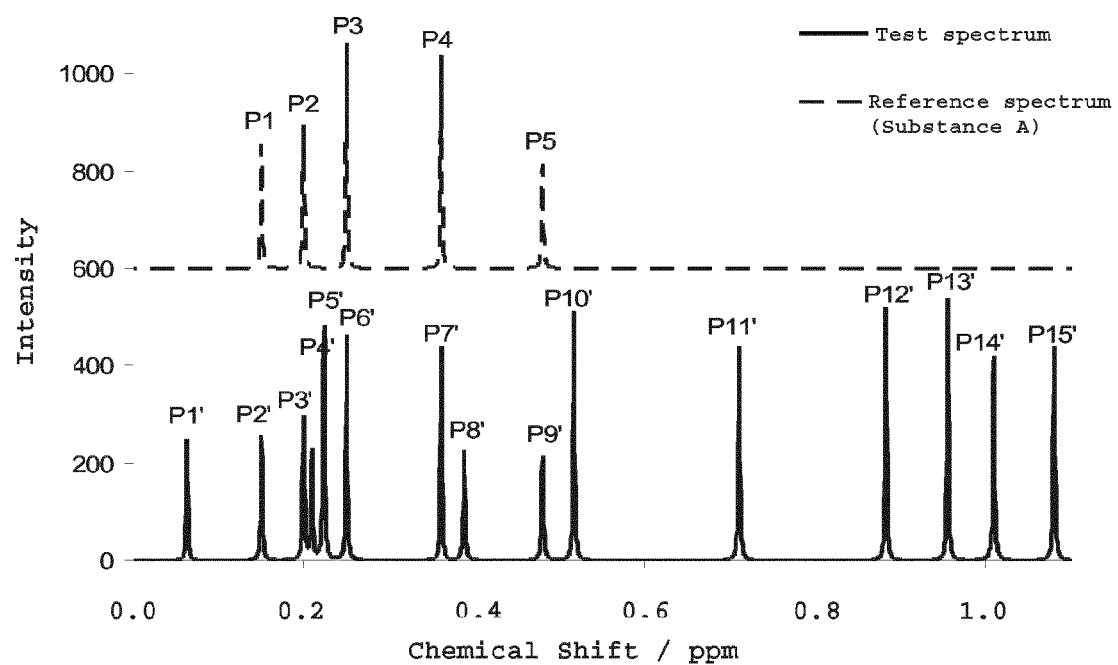
FIG. 3 shows a comparison of an NMR spectrum of a sample with the NMR spectrum of the substance A from FIG. 1.

FIG. 3 shows the NMR spectrum of substance A, already illustrated in FIG. 1, as NMR reference spectrum (upper curve, dashed line) as well as an NMR spectrum of a sample, referred to as test spectrum, which said sample contains a substance to be identified (lower curve, solid line). According to the manual evaluation methods known from prior art, one would search for the peaks contained in the NMR reference spectrum of substance A in the NMR spectrum of the sample with the substance to be identified by means of a visual comparison. In the present case, this would indeed still be possible due to the comparably low complexity of the NMR spectrum of the sample.

However, the present method, illustrated as an example, takes a different approach. Allocating peaks contained in the NMR spectrum of the sample to corresponding peaks in the NMR reference spectrum of substance A thus does not take place by means of a pattern matching. Rather, the integral ratio values and the distance values of the matrices illustrated in tables 2 to 4 are compared with each other. For this purpose, integral ratio values for all possible integral ratios, in each case from two integral values of the NMR spectrum of the sample, are now calculated. Additionally, all the distance values of in each case two peaks are calculated on the basis of corresponding position values for the NMR spectrum of the sample. This takes place in the manner already illustrated above for the NMR reference spectrum of substance A.

Afterwards, the integral ratio values of the NMR spectrum of the sample are compared with the integral ratio values of the NMR reference spectrum. In like manner, the distance values of the NMR spectrum of the sample are compared with the distance values of the NMR reference spectrum.

The subsequent table 5 shows the integral ratio values of the NMR spectrum of the sample calculated in such a way, wherein those integral ratio values which correspond to the integral ratio values of the NMR reference spectrum, are marked.

Table 5: Integral ratio values of the peaks of the NMR spectrum of the sample with marked correspondences to integral ratio values of the NMR reference spectrum.

TABLE 5

Integral ratio values of the peaks of the NMR spectrum of the sample with marked correspondences to integral ratio values of the NMR reference spectrum.

| Peak | Int. | P1' | P2' | P3' | P4' | P5' | P6' | P7' | P8' | P9' | P10' | P11' | P12' | P13' | P14' | P15' |
|---|---|---|---|---|---|---|---|---|---|---|---|---|---|---|---|---|
|  |  | 0.696 | 0.826 | 1.019 | 0.683 | 1.626 | 1.249 | 1.178 | 0.791 | 0.789 | 1.496 | 1.367 | 1.408 | 1.474 | 1.494 | 1.450 |
| P1' | 0.696 | 1 | 0.843 | 0.683 | 1.019 | 0.428 | 0.557 | 0.591 | 0.880 | 0.883 | 0.466 | 0.509 | 0.494 | 0.472 | 0.466 | 0.480 |
| P2' | 0.826 | 1.186 | 1 | 0.810 | 1.209 | 0.508 | 0.661 | 0.701 | 1.044 | 1.047 | 0.552 | 0.604 | 0.586 | 0.560 | 0.553 | 0.570 |
| P3' | 1.019 | 1.464 | 1.234 | 1 | 1.492 | 0.627 | 0.816 | 0.865 | 1.289 | 1.292 | 0.682 | 0.746 | 0.724 | 0.692 | 0.683 | 0.703 |
| P4' | 0.683 | 0.981 | 0.827 | 0.670 | 1 | 0.420 | 0.547 | 0.580 | 0.864 | 0.866 | 0.457 | 0.500 | 0.485 | 0.464 | 0.457 | 0.471 |
| P5' | 1.626 | 2.335 | 1.969 | 1.595 | 2.380 | 1 | 1.302 | 1.380 | 2.055 | 2.061 | 1.087 | 1.189 | 1.154 | 1.103 | 1.089 | 1.121 |
| P6' | 1.249 | 1.794 | 1.512 | 1.225 | 1.828 | 0.768 | 1 | 1.060 | 1.579 | 1.583 | 0.835 | 0.914 | 0.887 | 0.848 | 0.836 | 0.862 |
| P7' | 1.178 | 1.692 | 1.426 | 1.155 | 1.724 | 0.725 | 0.943 | 1 | 1.489 | 1.493 | 0.788 | 0.862 | 0.836 | 0.799 | 0.789 | 0.813 |
| P8' | 0.791 | 1.136 | 0.958 | 0.776 | 1.158 | 0.487 | 0.633 | 0.672 | 1 | 1.003 | 0.529 | 0.579 | 0.562 | 0.537 | 0.530 | 0.546 |
| P9' | 0.789 | 1.133 | 0.955 | 0.774 | 1.155 | 0.485 | 0.632 | 0.670 | 0.997 | 1 | 0.527 | 0.577 | 0.560 | 0.535 | 0.528 | 0.544 |
| P10' | 1.496 | 2.148 | 1.811 | 1.467 | 2.189 | 0.920 | 1.197 | 1.270 | 1.891 | 1.896 | 1 | 1.094 | 1.062 | 1.015 | 1.001 | 1.032 |
| P11' | 1.367 | 1.963 | 1.655 | 1.341 | 2.001 | 0.841 | 1.094 | 1.160 | 1.728 | 1.733 | 0.914 | 1 | 0.971 | 0.927 | 0.915 | 0.943 |
| P12' | 1.408 | 2.023 | 1.705 | 1.382 | 2.061 | 0.866 | 1.128 | 1.196 | 1.780 | 1.785 | 0.942 | 1.030 | 1 | 0.956 | 0.943 | 0.972 |
| P13' | 1.474 | 2.117 | 1.784 | 1.446 | 2.157 | 0.907 | 1.180 | 1.251 | 1.863 | 1.868 | 0.985 | 1.078 | 1.046 | 1 | 0.987 | 1.017 |
| P14' | 1.494 | 2.145 | 1.808 | 1.465 | 2.186 | 0.919 | 1.196 | 1.268 | 1.888 | 1.893 | 0.999 | 1.093 | 1.060 | 1.013 | 1 | 1.030 |
| P15' | 1.450 | 2.082 | 1.755 | 1.422 | 2.122 | 0.892 | 1.161 | 1.231 | 1.833 | 1.838 | 0.969 | 1.061 | 1.029 | 0.984 | 0.971 | 1 |

A correspondence of an integral ratio value of the NMR spectrum of the sample to a corresponding integral ratio value of the NMR reference spectrum was then assumed when the respective integral ratio values differed from each other by less than ±0.002. The values, marked diagonally hatched in table 5, represent a first subset from the integral ratio values. The non-significant values resulting from a division by themselves are marked by a horizontal hatching in this table—as in all the subsequent tables also.

In the subsequent table 6 all possible distance values between in each case two peaks on the basis of the corresponding position values of these peaks of the NMR spectrum of the sample are illustrated. As explained above, calculating the distance values can take place on the basis of differences or quotients. Distance values of the NMR spectrum of the sample which correspond to distance values of the NMR reference spectrum of substance A are again marked. It was proceeded on the assumption that there is a correspondence here when the distance values of the NMR spectrum of the sample differed from the distance values of the NMR reference spectrum by less than ±0.005.

TABLE 6

Distance values between in each case two peaks of the NMR spectrum of the sample with marked correspondences to distance values of the NMR reference spectrum.

| Peak | ppm | P1' | P2' | P3' | P4' | P5' | P6' | P7' | P8' | P9' | P10' | P11' | P12' | P13' | P14' | P15' |
|---|---|---|---|---|---|---|---|---|---|---|---|---|---|---|---|---|
| | | 0.063 | 0.151 | 0.200 | 0.210 | 0.224 | 0.251 | 0.362 | 0.389 | 0.481 | 0.518 | 0.712 | 0.884 | 0.957 | 1.011 | 1.082 |
| P1' | 0.063 | | -0.088 | -0.137 | -0.147 | | -0.188 | -0.299 | | -0.418 | -0.455 | -0.649 | -0.821 | -0.894 | -0.948 | -1.019 |
| P2' | 0.151 | 0.088 | | | -0.059 | -0.073 | | | -0.238 | | -0.367 | -0.561 | -0.734 | -0.806 | -0.860 | -0.931 |
| P3' | 0.200 | 0.137 | | | -0.009 | -0.024 | | | -0.189 | | -0.318 | -0.512 | -0.684 | -0.757 | -0.811 | -0.882 |
| P4' | 0.210 | 0.147 | 0.059 | 0.009 | | -0.014 | -0.041 | -0.152 | -0.179 | -0.271 | -0.308 | -0.502 | -0.675 | -0.747 | -0.801 | -0.872 |
| P5' | 0.224 | | 0.073 | 0.024 | 0.014 | | -0.027 | -0.138 | | -0.257 | -0.294 | -0.488 | -0.661 | -0.733 | -0.787 | -0.858 |
| P6' | 0.251 | 0.188 | | | 0.041 | 0.027 | | | -0.138 | | -0.267 | -0.461 | -0.634 | -0.706 | -0.760 | -0.831 |
| P7' | 0.362 | 0.299 | | | 0.152 | 0.138 | | | -0.027 | | -0.156 | -0.350 | -0.523 | -0.595 | -0.649 | -0.720 |
| P8' | 0.389 | | 0.238 | 0.189 | 0.179 | | 0.138 | 0.027 | | -0.092 | -0.129 | -0.323 | -0.496 | -0.568 | -0.622 | -0.693 |
| P9' | 0.481 | 0.418 | | | 0.271 | 0.257 | | | 0.092 | | -0.037 | | -0.404 | -0.476 | -0.530 | -0.601 |
| P10' | 0.518 | 0.455 | 0.367 | 0.318 | 0.308 | 0.294 | 0.267 | 0.156 | 0.129 | 0.037 | | -0.194 | -0.367 | -0.439 | -0.493 | -0.564 |
| P11' | 0.712 | 0.649 | 0.561 | 0.512 | 0.502 | 0.488 | 0.461 | 0.350 | 0.323 | | 0.194 | | -0.173 | -0.245 | -0.299 | -0.370 |
| P12' | 0.884 | 0.821 | 0.734 | 0.684 | 0.675 | 0.661 | 0.634 | 0.523 | 0.496 | 0.404 | 0.367 | 0.173 | | -0.073 | -0.127 | -0.198 |
| P13' | 0.957 | 0.894 | 0.806 | 0.757 | 0.747 | 0.733 | 0.706 | 0.595 | 0.568 | 0.476 | 0.439 | 0.245 | 0.073 | | | -0.125 |
| P14' | 1.011 | 0.948 | 0.860 | 0.811 | 0.801 | 0.787 | 0.760 | 0.649 | 0.622 | 0.530 | 0.493 | 0.299 | 0.127 | | | -0.071 |
| P15' | 1.082 | 1.019 | 0.931 | 0.882 | 0.872 | 0.858 | 0.831 | 0.720 | 0.693 | 0.601 | 0.564 | 0.370 | 0.198 | 0.125 | 0.071 | |

The distance values marked with diagonal hatching in table 6 represent a second subset of values.

Now, upon comparing the values of table 5 with the values of table 6 and filtering for all those values which were formed from the same spectral values and are marked in both table 5 and also table 6, the result illustrated in table 7 is obtained.

TABLE 7

Visualization of values of the first subset and the second subset formed from the same spectral values.

| Peak | P1' | | | P4' | P5' | | | P8' | | P10' | P11' | P12' | P13' | P14' | P15' |
|---|---|---|---|---|---|---|---|---|---|---|---|---|---|---|---|
| P1' | ▨ | | | | | | | | | | | | | | |
| | | ▨ | ▨ | | ▨ | | | ▨ | | | | | | | |
| | | ▨ | ▨ | | ▨ | | | ▨ | | | | | | | |
| P4' | | | | ▨ | | | | | | | | | | | |
| P5' | | | | | ▨ | | | | | | | | | | |
| | | ▨ | ▨ | | | | | ▨ | | | | | | | |
| | | ▨ | ▨ | | | | | ▨ | | | | | | | |
| P8' | | | | | | | | ▨ | | | | | | | |
| | | ▨ | ▨ | | | | | | | | | | | | |
| P10' | | | | | | | | | | ▨ | | | | | |
| P11' | | | | | | | | | | | ▨ | | | | |
| P12' | | | | | | | | | | | | ▨ | | | |
| P13' | | | | | | | | | | | | | ▨ | | |
| P14' | | | | | | | | | | | | | | ▨ | |
| P15' | | | | | | | | | | | | | | | ▨ |

The values marked with diagonal hatching in table 7 represent the intersection between the first subset and the second subset and can be referred to as third subset. When all the columns and rows which are not marked are now deleted from table 7, one can directly correlate the individual peaks of the NMR spectrum of the sample with the individual peaks of the NMR reference spectrum. This correlation or allocation is illustrated in the subsequent table 8.

TABLE 8

Allocation of the peaks of substance A in the NMR spectrum of the sample to the peaks of substance A in the NMR reference spectrum.

| Peaks of substance A in the reference spectrum | Peaks of substance A in the test spectrum |
|---|---|
| P1 | P2' |
| P2 | P3' |

TABLE 8-continued

Allocation of the peaks of substance A in the NMR spectrum of the sample to the peaks of substance A in the NMR reference spectrum.

| Peaks of substance A in the reference spectrum | Peaks of substance A in the test spectrum |
|---|---|
| P3 | P6' |
| P4 | P7' |
| P5 | P9' |

In the present exemplary embodiment of a method for substance identification 100% of the peaks or spectral values of substance A in the NMR reference spectrum could therefore also be found again in the NMR spectrum of the sample. Consequently, an unequivocal identification of a component of the sample as substance A can take place. Insofar as the further composition of the sample shall be clarified, a further run through the previously specified method would now have to take place, wherein then another NMR reference spectrum would be used for comparison.

Apart from a qualitative determination of the substance contained in the sample as substance A, moreover, a quantitative statement about the concentration of substance A contained in the sample is possible on the basis of the measured NMR spectrum.

While previously a peak from the NMR spectrum of the sample Pj' was allocated to each peak of the reference substance Pi (i=1, 2, ..., 5), now from each individual one of these allocated peaks the concentration $\Gamma_{Pj'}^A$ (in mg/ml) of substance A in the NMR spectrum of the sample can be calculated by means of the following equation, wherein $\Gamma_{Ref}^A$ (in mg/ml) is the concentration of substance A in the reference spectrum (Ref):

$$\Gamma_{Pj'}^A [\text{mg/ml}] = \frac{I(Pi)}{I(Pj')} \cdot \Gamma_{Ref}^A [\text{mg/ml}]$$

Figure 4:
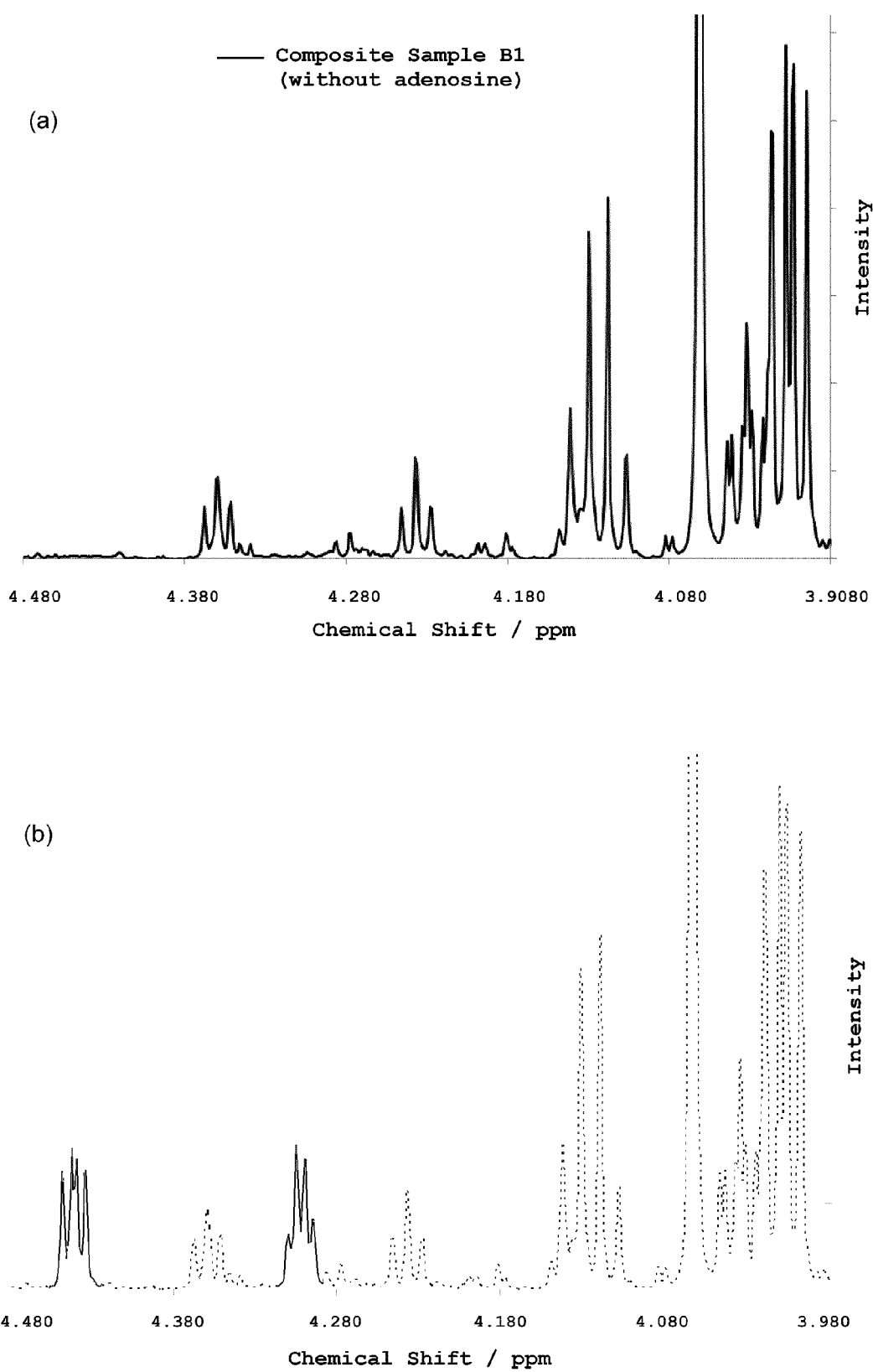
FIG. 4A shows an NMR spectrum of a composite sample B1 without adenosine.
FIG. 4B shows an NMR spectrum of a composite sample B1 with adenosine and FIG. 5 shows a graphic illustration of the frequency distribution of the adenosine concentration, detected on the basis of the NMR spectrum of FIG. 4B.

FIG. 4A shows an NMR spectrum of a composite sample B1 composed of seven different individual substances. The composite sample B1 here does not contain adenosine. FIG. 4B shows an NMR spectrum of the same composite sample B1, to which, however, as eighth substance 0.5 mg/ml adenosine has been added. The peaks which are to be attributed to adenosine are illustrated in black, while the peaks which are to be attributed to the remaining seven substances are illustrated with a dashed line. In both NMR spectra of FIG. 4 the intensity is again plotted against the chemical shift (measured in ppm).

In the composite sample B1 the peaks caused by adenosine were identified by means of an NMR reference spectrum of adenosine by performing the previously specified method of substance identification. The adenosine concentration in the composite sample B1 was afterwards determined from each peak allocated to the substance adenosine. For this purpose the previously explained formula was used, wherein the adenosine concentration of the adenosine solution used for creating the NMR reference spectrum of adenosine was known.

Figure 5:
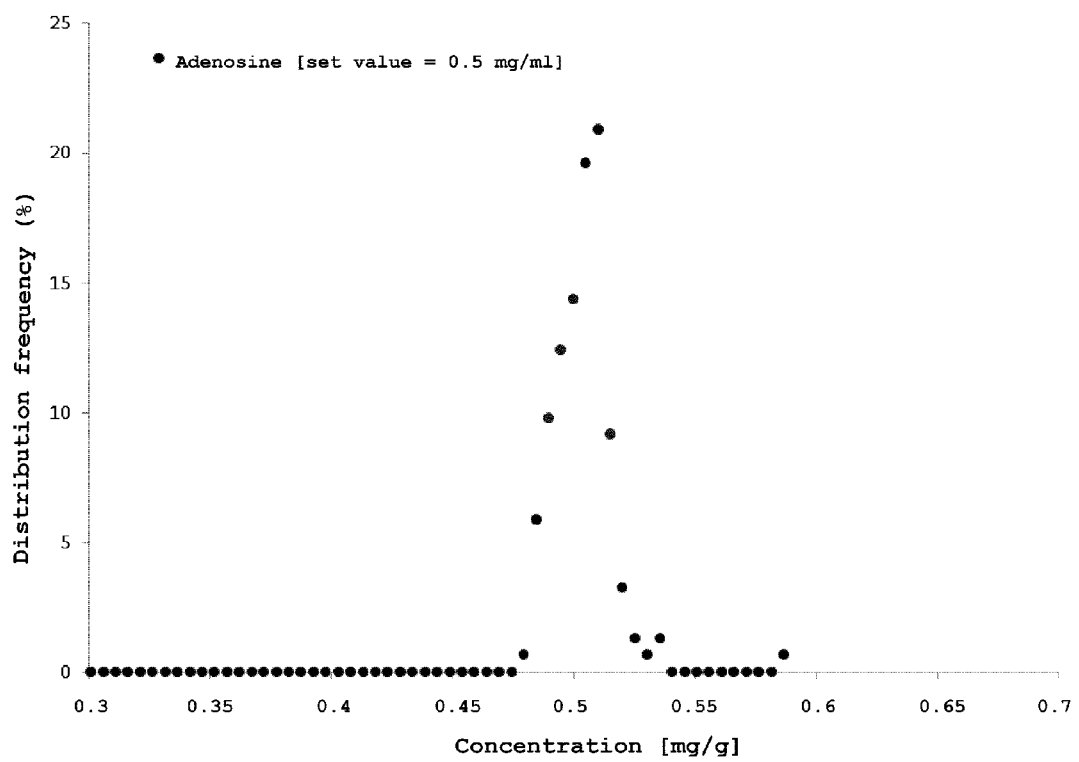

FIG. 5 shows the frequency distribution of the adenosine concentration in the composite sample B1 detected in this manner. It is noticeable here that the measured value of 0.5075 mg/ml which was most often detected deviated from the set value of 0.5 mg/ml only by 1.5%. This shows that a quantitative substance identification with the presently specified method is possible with very high accuracy.

In order to be able to detect the accuracy not only for adenosine, all the seven individual substances of the composite sample B1 were determined with the previously specified method, first qualitatively and afterwards quantitatively. The corresponding quantification results are illustrated in the subsequent table 9. The specification "set value" here refers to the concentration of the respective substance actually contained in the composite sample B1. Said concentration was exactly detected upon composition of the composite sample B1 to in this way be able to make statements about the accuracy of the present quantification method.

TABLE 9

Quantification results of all the individual substances present in the composite sample B1 (without adenosine)

| Substance | Set value [mg/ml] | Measured value [mg/ml] | Deviation [%] |
|---|---|---|---|
| Adenosine | 0 | 0.000 | 0.00 |
| Leucine | 0.186 | 0.195 | 4.84 |
| Benzoate | 0.084 | 0.084 | 0.00 |
| Lactate | 0.375 | 0.403 | 7.47 |
| Uridine | 0.153 | 0.15 | 1.96 |
| Creatinine | 0.542 | 0.575 | 6.09 |
| Phenylalanine | 0.896 | 0.91 | 1.56 |
| Glucose | 0.893 | 0.852 | 4.59 |

TABLE 10

Quantification results of all the individual substances present in the composite sample B1 (with adenosine).

| Substance | Set value [mg/ml] | Measured value [mg/ml] | Deviation [%] |
|---|---|---|---|
| Adenosine | 0.5 | 0.508 | 1.50 |
| Leucine | 0.186 | 0.195 | 4.84 |
| Benzoate | 0.084 | 0.084 | 0.00 |
| Lactate | 0.375 | 0.403 | 7.47 |
| Uridine | 0.153 | 0.15 | 1.96 |
| Creatinine | 0.542 | 0.575 | 6.09 |
| Phenylalanine | 0.896 | 0.91 | 1.56 |
| Glucose | 0.893 | 0.52 | 4.59 |

To be able to make extensive statements about the accuracy of the presently specified quantification method, numerous individual substances were provided as solutions with a concentration of 0.1 mg/ml each and were measured by NMR spectroscopy. Afterwards, a comparison of the NMR spectra detected in this manner with corresponding NMR reference spectra of the same substances of other concentration took place. The measured value detected in this manner was afterwards compared to the set value to calculate a measurement error. It is noticeable here that the measurement error regularly lies in the lower single-digit percent range and always stays considerably below 10%. This proves the high accuracy of the presently specified quantification method.

TABLE 11

Quantification results of different individual substances.

| Substance | Set value [mg/ml] | Measured value [mg/ml] | Uncertainty [mg/ml] | Deviation [%] |
|---|---|---|---|---|
| Acetic acid | 0.1 | 0.1089 | 0.001 | 8.90 |
| Formic acid | 0.1 | 0.0977 | 0.001 | 2.30 |
| Propionic acid | 0.1 | 0.096 | 0.002 | 4.00 |
| Butyric acid | 0.1 | 0.099 | 0.0005 | 1.00 |

TABLE 11-continued

Quantification results of different individual substances.

| Substance | Set value [mg/ml] | Measured value [mg/ml] | Uncertainty [mg/ml] | Deviation [%] |
|---|---|---|---|---|
| Isobutyric acid | 0.1 | 0.109 | 0.0005 | 9.00 |
| Valeric acid | 0.1 | 0.105 | 0.0015 | 5.00 |
| Isovaleric acid | 0.1 | 0.091 | 0.0005 | 9.00 |
| Phenylacetic acid | 0.1 | 0.1043 | 0.0015 | 4.30 |
| Benzoic acid | 0.1 | 0.103 | 0.0005 | 3.00 |
| Ethanol | 0.1 | 0.096 | 0.001 | 4.00 |
| Methanol | 0.1 | 0.1033 | 0.001 | 3.30 |
| Butanol | 0.1 | 0.1 | 0.0025 | 0.00 |
| Propanol | 0.1 | 0.105 | 0.0025 | 5.00 |
| 2-Butanol | 0.1 | 0.0985 | 0.0005 | 1.50 |
| Glycerine | 0.1 | 0.1035 | 0.0015 | 3.50 |
| Acetone | 0.1 | 0.0911 | 0.0009 | 8.90 |
| Formaldehyde | 0.1 | 0.0991 | 0.001 | 0.90 |
| Acetaldehyde | 0.1 | 0.108 | 0.001 | 8.00 |
| Isopropanol | 0.1 | 0.102 | 0.003 | 2.00 |
| Succinic acid | 0.1 | 0.1 | 0.001 | 0.00 |
| Citric acid | 0.09 | 0.975 | 0.001 | 8.33 |
| Glutamine | 0.1 | 0.101 | 0.001 | 1.00 |
| Alanine | 0.1 | 0.105 | 0.0015 | 5.00 |
| Valine | 0.1 | 0.109 | 0.001 | 9.00 |
| Glucose | 0.1 | 0.1033 | 0.0035 | 3.30 |
| Acetylcysteine | 0.1 | 0.099 | 0.006 | 1.00 |
| 2-furoic acid | 0.1 | 0.098 | 0.007 | 2.00 |
| Syringic acid | 0.1 | 0.1005 | 0.0005 | 0.50 |
| 4-hydroxybenzaldehyde | 0.1 | 0.0985 | 0.0005 | 1.50 |
| 4-hydroxybenzoic acid | 0.1 | 0.102 | 0.006 | 2.00 |
| Vanillic acid | 0.1 | 0.098 | 0.001 | 2.00 |
| Indole | 0.1 | 0.1025 | 0.0025 | 2.50 |
| 2,6-Dimethoxyphenol | 0.1 | 0.099 | 0.0005 | 1.00 |
| Monomethylamine | 0.1 | 0.1006 | 0.001 | 0.60 |
| Dimethylamine | 0.1 | 0.103 | 0.001 | 3.00 |
| Trimethylamine | 0.1 | 0.0957 | 0.001 | 4.30 |
| Pyruvic acid | 0.1 | 0.095 | 0.0005 | 5.00 |

Through a combination of the quantification method with the previously explained method of identification it is therefore possible not only to be able to unequivocally identify individual substances as specific substances, but also to be able to make precise statements about the concentration of these substances in a composite sample.

The exemplary embodiments of the method claimed, which are presently illustrated as examples, can in the scope of the explanations above be varied in any kind of manner and are not to be understood as a restriction of the subject-matter claimed.

The invention claimed is:

1. A method for the identification of a substance in a sample, comprising the following steps:
   a) providing an NMR spectrum of a sample containing at least one substance having at least one NMR-active nucleus,
   b) converting the NMR spectrum into discrete spectral values, wherein each spectral value has an integral value, specifying the height and/or the area of an individual line of the NMR spectrum or of an individual spectral section of the NMR spectrum, and a position value, specifying the mean position of the line considered or of the considered spectral section in the NMR spectrum,
   c) determining a multitude of integral ratio values, in each case from two integral values of the NMR spectrum, wherein each integral ratio value specifies the ratio of the height and/or of the area of the underlying spectral values,
   d) determining a multitude of distance values, in each case from two position values of the NMR spectrum, wherein each distance value specifies the spectral distance between the underlying spectral values,
   d) comparing the integral ratio values of the NMR spectrum with corresponding integral ratio values of an NMR reference spectrum of at least one reference substance,
   f) selecting a first proper subset from the integral ratio values of the NMR spectrum, wherein the first subset comprises those integral ratio values which correspond to an integral ratio value of the NMR reference spectrum within first tolerance limits that can be given in each case,
   g) comparing the distance values of the NMR spectrum with corresponding distance values of the NMR reference spectrum,
   h) selecting a second proper subset from the distance values of the NMR spectrum, wherein the second subset comprises those distance values which correspond to a distance value of the NMR reference spectrum within second tolerance limits that can be given in each case,
   i) comparing the first subset with the second subset and selecting those integral ratio values and distance values from both subsets as third proper subset which were formed from the same spectral values,
   j) deciding whether the substance contained in the sample is identified as the reference substance, with the help of a quality criterion of the values of the third subset, said criterion being determined by comparing these values with the integral ratio values and/or the distance values of the NMR reference spectrum.

2. The method according to claim 1, wherein the NMR reference spectrum is an NMR spectrum of exactly one reference substance.

3. The method according to claim 1, wherein the quality criterion comprises a measure for the deviation of the integral ratio values of the NMR spectrum from the integral ratio values of the NMR reference spectrum and/or the deviation of the distance values of the NMR spectrum from the distance values of the NMR reference spectrum.

4. The method according to claim 1, wherein the quality criterion comprises ,a measure for the number of values of the third subset in comparison with the number of integral ratio values or of distance values of the NMR reference spectrum.

5. The method according to claim 1, wherein steps e) to j) are repeated often with further NMR reference spectra of other reference substances until the substance contained in the sample is identified as a reference substance or until there are no further NMR reference spectra.

6. The method according to claim 1, wherein the distance values are calculated as direct differences of the position values, as standardized differences of the position values or as quotient of the position values.

7. The method according to claim 1, wherein the substance contained in the sample is identified quantitatively.

8. The method according to claim 1, wherein the method is performed by using a decoupled NMR spectrum and, when the substance is not unequivocally identified, is performed again by using a non-decoupled NMR spectrum of the same sample.

9. A computer program product for the identification of a substance in a sample wherein an NMR spectrum of the sample containing at least one substance having at least one NMR-active nucleus has been provided, comprising a non-transitory computer-readable medium having program instructions that, when executed, cause a processor to perform the steps of:

a) converting the NMR spectrum into discrete spectral values, wherein each spectral value has an integral value, specifying the height and/or the area of an individual line of the NMR spectrum or of an individual spectral section of the NMR spectrum, and a position value, specifying the mean position of the line considered or of the considered spectral section in the NMR spectrum,
b) determining a multitude of integral ratio values, in each case from two integral values of the NMR spectrum, wherein each integral ratio value specifies the ratio of the height and/or of the area of the underlying spectral values,
c) determining a multitude of distance values, in each case from two position values of the NMR spectrum, wherein each distance value specifies the spectral distance between the underlying spectral values,
d) comparing the integral ratio values of the NMR spectrum with corresponding integral ratio values of an NMR reference spectrum of at least one reference substance,
e) selecting a first proper subset from the integral ratio values of the NMR spectrum, wherein the first subset comprises those integral ratio values which correspond to an integral ratio value of the NMR reference spectrum within first tolerance limits that can be given in each case,
f) comparing the distance values of the NMR spectrum with corresponding distance values of the NMR reference spectrum,
g) selecting a second proper subset from the distance values of the NMR spectrum, wherein the second subset comprises those distance values which correspond to a distance value of the NMR reference spectrum within second tolerance limits that can be given in each case,
h) comparing the first subset with the second subset and selecting those integral ratio values and distance values from both subsets as third proper subset which were formed from the same spectral values, and
i) deciding whether the substance contained in the sample is identified as the reference substance, with the help of a quality criterion of the values of the third subset, said criterion being determined by comparing these values with the integral ratio values and/or the distance values of the NMR reference spectrum.

* * * * *